US00PP18740P2

(12) United States Plant Patent
Carruth

(10) Patent No.: US PP18,740 P2
(45) Date of Patent: Apr. 22, 2008

(54) CLIMBING ROSE PLANT NAMED 'WEKPUROST'

(50) Latin Name: *Rosa hybrida*
Varietal Denomination: WEKpurosot

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 46 days.

(21) Appl. No.: 11/598,457

(22) Filed: Nov. 13, 2006

(51) Int. Cl.
*A01H 5/00* (2006.01)

(52) U.S. Cl. ..... Plt./109

(58) Field of Classification Search ..... Plt./109
See application file for complete search history.

(56) References Cited

U.S. PATENT DOCUMENTS

PP16,623 P3 6/2006 Carruth

*Primary Examiner*—Wendy Haas
(74) *Attorney, Agent, or Firm*—McKee, Voorhees & Sease, P.L.C.

(57) ABSTRACT

A new variety of Climbing rose suitable for garden decoration, having flowers of wine purple coloration.

1 Drawing Sheet

CLASSIFICATION:

The present invention relates to a new *Rosa hybrida* plant.

Variety denomination:

The new plant has the varietal denomination 'WEKpurosot'.

BACKGROUND OF THE INVENTION

This invention relates to a new and distinct variety of Climbing Rose. It has an undisseminated seedling of the inventor's creation as its seed parent with following genetic origin (International 'Herald Tribune'×*Rosa soulieana* derivative)×('Sweet Chariot'×'Blue Nile') and as its pollen parent the variety known as 'WEKtorroc' (not patented).

SUMMARY OF THE INVENTION

Among the features which distinguish the new variety from other presently available and commercial rose cultivars known to the inventor are the following combination of characteristics: its numerous hairs on the peduncles, styles, rachis and flower receptacles, its strong citrus-like and spicy flower fragrance, its very long foliaceous appendages on the surface of the bud, its unusual wine purple flower coloration and its heavy red suffusion on the stipules. The plant has a spreading climbing growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKpurosot' may be asexually propagated by cuttings, budding and grafting. The budding and grafting successfully occurred on the plant/rootstock *Rosa hybrida* cv. 'Dr. Huey' (unpatented).

COMPARISON WITH PARENTS

The new rose may be distinguished from its seed parent, an undisseminated seedling of the inventor's creation by the following combination of characteristics: whereas 'WEKpurosot' bears medium sized flowers (about 7.3 to about 9.8 cm. in diameter) of wine purple coloration, the undisseminated seedling bears significantly smaller flowers of lavender coloration. The new variety is classified as a climbing rose with a spreading climbing growing habit, whereas the seed parent is a floribunda rose with a significantly shorter and more compact growing habit.

The new variety may be distinguished from its pollen parent, 'WEKtorroc' (U.S. Plant Pat. No. 16,623) by the following combination of characteristics: whereas 'WEKpursor' bears semi-double flowers (about 10 to 13 petals) of wine purple coloration, 'WEKtorroc' bears double flowers of deep pink striped white coloration with significantly heavier petalage (about 17 to 25 peals). The new variety bears flowers with a strong citrus-like and spicy fragrance, whereas the pollen parent bears flowers with a significantly lighter fragrance.

COMPARISON WITH THE CLOSEST COMMERCIALLY AVAILABLE CULTIVAR

The new variety may be distinguished from its closest commercially available cultivar, 'WEKfabpur' by the following combination of characteristics: whereas 'WEKpurosot' bears medium sized flowers (about 7.3 to about 9.8 cm. in diameter) of wine purple coloration, 'WEKfabpur' bears significantly smaller flowers (about 5.3 to about 7.4 cm. in diameter) of velvety black purple coloration with a white eye. The new variety is classified as a climbing rose with a spreading climbing growing habit with canes about 250 to about 380 cm. in length, whereas the closest commercially available cultivar is classified as a shrub rose with a bushy compact and significantly shorter growing habit (about 75 to about 92 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966), except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

BOTANICAL DESIGNATION

The new variety botanical designation is *Rosa hybrida* 'WEKpurosot'.

FLOWER

The new variety usually bears its flowers in clusters of five to eight or more per stem. Flowers are borne in regular rounded clusters on strong medium to long stems (about 36 to about 105 cm.). Outdoors, the plant blooms abundantly and nearly continuously during the growing season. The flowers have a strong citrus-like and spicy fragrance.

BUD

The peduncle is about 2.7 to about 4.0 cm. in length, of average caliper (about 0.2 to about 0.3 cm. in diameter), and usually erect. It is entirely smooth with numerous hairs. Peduncle color is between 144A and 146C often moderately suffused, especially on the side exposed to the sun, with between 187B and 183B.

Before the calyx breaks, the bud is about 0.8 to about 1.4 cm. in diameter at the widest point, about 1.4 to about 1.8 cm. in length, and pointed to somewhat ovoid in shape with a moderately conspicuous neck. The surface of the bud bears few very long foliaceous appendages and some hairs, usually with slender entire foliaceous parts extending beyond the tip of the bud about ¼ or more of its length. Bud color is between 144A and 146C often moderately suffused, especially on the side exposed to the sun, with between 187A and 183A.

The sepals are about 1.9 to about 2.8 cm. in length and about 0.5 to about 0.7 cm. in width at the widest point. The outer surface color of the sepal is between 144A and 146C often moderately suffused, especially on the side exposed to the sun, with between 187A and 183A. The inner surface color of the sepal is between 137A and 138B and covered with fine wooly tomentum; sepal margins are lined with some stipitate glands and numerous hairs.

The receptacle of the flower is of medium length (about 0.5 to about 0.8 cm.) and somewhat heavy in caliper (about 0.4 to about 0.7 cm. in diameter). The receptacle is globular to somewhat rounded in form. Its surface is very smooth with numerous hairs and with thick fleshy walls. The receptacle color is between 144A and 146C often moderately suffused, especially on the side exposed to the sun, with between 187B and 183B.

As the petals open (after the calyx breaks), the bud is about 1.3 to about 1.8 cm. in diameter at the widest point, about 1.5 to about 2.5 cm. in length, and moderately ovoid to somewhat pointed in form. The color of the under surfaces of the newly opened petals is near 187D at the lower third of the petal gradually suffusing to between 187B and 59B toward the remaining surface of the petal usually showing a petal edge as dark as near 187A. At the point where the petal attaches, there is a moderately small zone of between 1C and 3C.

At the point where the petal attaches on the upper surfaces of the newly opened petals, there is a somewhat large zone of between 7A and 9A. Surrounding that attachment zone is a moderately defined zone of between 59C and 60B that gradually suffuses to between 187B and 59B toward the center of the petal that continues to suffuse to darker than near 187A on the upper two-thirds of the petal.

BLOOM

When fully open, the bloom ranges from about 7.3 to about 9.8 cm. in diameter. Petalage is semi-double with about 10 to 13 petals and about 1 to 3 petaloids irregularly arranged. When partially open, the bloom from is cupped to somewhat globular, and the petals are loosely spiraled to cupped to somewhat undulated with petal edges slightly reflexed outward. When fully open, the bloom form is more cupped, and the petals are loosely cupped to somewhat undulated with petal edges slightly reflexed outward.

PETALS

The substance of the petals is moderately heavy and of medium to thick thickness, with upper surfaces velvety to moderately satiny and under surfaces very shiny. The petals are about 2.9 to about 5.1 cm. in length and about 3.1 to about 5.2 cm. in width at the widest point. Petal margins are entire.

The outer petals are nearly rounded to somewhat obovate in shape with rounded to sometimes retuse apices.

The inner petals are broadly rounded to moderately obovate the in shape with rounded apices.

Petaloids are about 2.2 to about 3.3 cm. in length and about 2.0 to about 3.4 cm. in width at the widest point. Petaloids are irregularly shaped moderately small zone of between 1D and 3D.

At the point where the petal attaches on the upper surfaces of the outer, intermediate and inner petals, there is a somewhat large one of between 6C and 7C. Surrounding that attachment zone is a moderately defined zone of between 60C and 64B that gradually suffuses to between 59B and 64B toward the center of the petal that continues to suffuse to between 79A and 60A on the upper two-thirds of the petal.

The under and upper surface color of the petaloids are similar in coloration to the upper and under surfaces of the outer, intermediate and inner petals.

The general tonality of the newly opened flower is between 59B and 64B that suffuses to between 79A and 60A on the outer two-thirds of the flower.

THREE-DAY-OLD FLOWER

The under surface color of the outer, intermediate and inner petals is between 72A and 74B gradually suffusing toward the petal edge with as dark as between 79A and 71B. At the point where the petal attaches, there is a large zone of between 4D and 155A.

At the point where the petal attaches on the upper surfaces of the outer, intermediate and inner petals, there is a somewhat large zone of between 155A and 4D. Surrounding that attachment zone is a moderately defined zone of between 81D and 69D that gradually suffuses to between 72A and 71C toward the center of the petal that continues to suffuse to between 79A and 72A on the upper two-thirds of the petal.

The under and upper surface color of the petaloids are similar in coloration to the upper and under surfaces of the outer, intermediate and inner petals.

The general tonality of the three-day-old flower is between 72A and 71C that suffuses to between 79A and 72A on the outer two-thirds of the flower.

On the spent bloom, the petals usually drop off cleanly.

In October in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 120) and are arranged regularly about the pistils; a few are mixed with petaloids. The filaments are of medium to long length (about 0.5 to about 1.5 cm.) most with anthers. Filaments are between 6C and 7C in color sometimes very lightly suffused with near 44D. The anthers are moderately small for the class and all open approximately at the same time. Anther color is near 17A on the external part and near 15D on the internal part when immature. Anther color at maturity is near 164C on the external part and near 200A on the internal part. Pollen is very abundant and between 16A and 15B in color.

FEMALE REPRODUCTIVE ORGANS

Pistils vary in number (average about 40). The styles are moderately even, very short in length (about 0.2 to about 0.4 cm.), average in caliper, and somewhat loosely bunched. Stigma color is between 14D and 20C. Style color is between 4D and 8D usually heavily suffused with near 53A. The styles are moderately covered with fine hairs. Ovaries are usually all enclosed in the calyx.

Hips are of average length (about 1.1 to about 1.5 cm.), very rounded to somewhat globular in form, and between 28A and 30A in color when ripe. The hip surface is very smooth with some hairs and with thick fleshy walls. The sepals are somewhat permanent and usually straight in shape.

The seeds are irregularly rounded, smooth in texture, approximately 10 to about 18 per hip, about 0.3 to about 0.5 cm. in diameter at the widest point and between 161B and 162C in color.

FOLIAGE

The compound leaves are usually comprised of three to seven leaflets and are borne abundantly. The seven-leaflet leaves are about 9.8 to about 18.4 cm. in length and about 7.4 to about 14.2 cm. in width at the widest point, moderately leathery to somewhat crisp in texture and semi-glossy in finish. The terminal leaflets are about 4.4 to about 7.6 cm. in length and about 2.5 to about 5.3 cm. in width at the widest point, shaped moderately ovate to somewhat oval with acute apices and rounded to slightly acute bases. Their margins are usually simply serrate.

The upper surface color of the mature leaf is between 137A and 143A. The under surface color of the mature leaf is between 146B and 147C. The upper surface color of the young leaf is between 146A and 144A, often moderately suffused with between 187A and 183A. The under surface color of the young leaf is between 146C and 144A, often moderately suffused with between 187B and 183A.

The rachis is average to somewhat heavy in caliper and moderately rough. The upper side is moderately grooved with numerous hairs and some stipitate glands on the edges of the grooves. The under side of the rachis is moderately rough with numerous hairs and few small prickles. The rachis color is near 146D on the under side and near 146B on the upper side, often moderately suffused especially on the young leaf with between 187A and 183A.

The stipules are about 1.2 to about 2.7 cm. in length and moderately wide (about 0.5 to about 0.8 cm.) with moderately long straight points that usually turn out at an angle of more than 45 degrees and often recurve toward the stem. The stipules color is between 137C and 146B often heavily suffused especially on the young leaf with between 187A and 187B.

The petiole is average to somewhat heavy in caliper and moderately rough. The upper side is moderately grooved with numerous hairs and some stipitate glands on the edges of the grooves. The under side of the petiole is moderately rough with numerous hairs and few small prickles. The petiole is about 0.4 to about 1.5 cm. in length and about 0.2 to about 0.3 cm in diameter at the widest point. The petiole color is near 146D on the under side and near 146B on the upper side, often moderately suffused especially on the young leaf with between 187A and 183A.

The plant displays on above average degree of resistance to powdery mildew and rust as compared to other commercial varieties grown under comparable conditions in Upland, Calif. The plant's winter hardiness and drought/heat tolerance are yet to be determined.

GROWTH

The plant has a spreading climbing growing habit with canes about 250 to about 380 cm. in length with full branching. It displays very vigorous growth and the canes are of somewhat heavy caliper for the class.

The color of the major stems is between 152B and 147B. They bear some large prickles that are about 1.0 to about 1.4 cm in length. The large prickles are slightly hooked downward with a somewhat long broad oval base; prickle and color is between 164A and 166C. The major stem bears no small prickles.

The color of the branches 146B and 146C sometimes moderately suffused with between 187B and 183A. They bear some large prickles which are of similar shape to the large prickles on the major stems. Prickles are about 0.4 to about 0.6 cm. in length. The color is between 166C and 165C. The branches bear no small prickles. The branches sometimes bear some fine hairs.

The color of the new shoots is between 144A and 146D often heavily suffused with between 187B and 183A. They bear some large prickles which are of similar shape to the large prickles on the major stems. Prickles are about 0.5 to about 0.8 cm. in length. The color is between 160B and 151C usually heavily suffused with between 187A and 187B. The shoots bear no small prickles. The new shoots sometimes bear some fine hairs.

I claim:

1. A new and distinct Climbing rose plant of the variety substantially as described and illustrated herein.

* * * * *

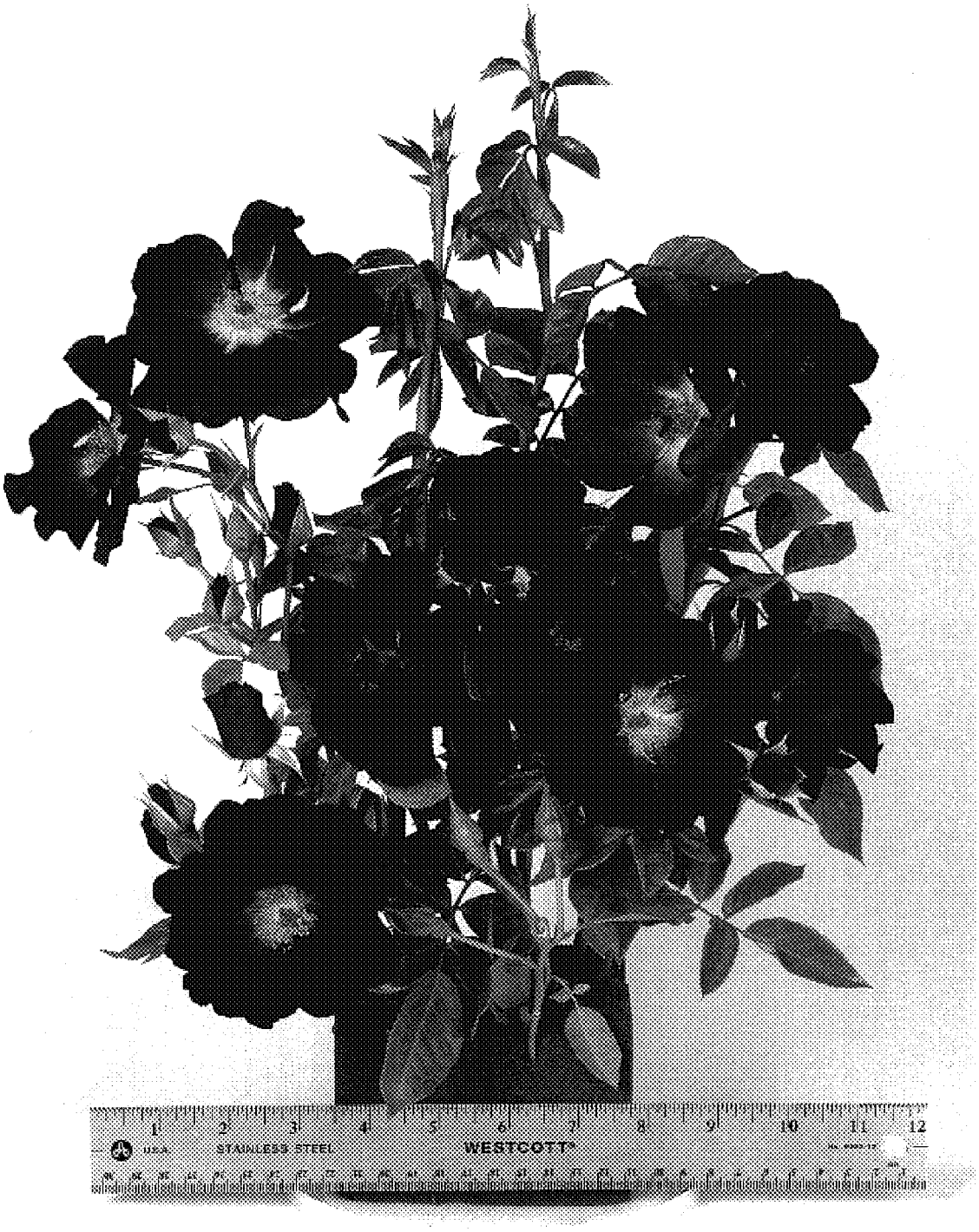
1 2 3 4 5 6 7 8 9 10 11 12
STAINLESS STEEL
WESTCOTT

UNITED STATES PATENT AND TRADEMARK OFFICE

CERTIFICATE OF CORRECTION

PATENT NO. : PP 18,740 P2
APPLICATION NO. : 11/598457
DATED : April 22, 2008
INVENTOR(S) : Thomas F. Carruth It is certified that error appears in the above-identified patent and that said Letters Patent is hereby corrected as shown below:

Title Page
Col. 1, Line (54):
DELETE after NAMED "'WEKPUROST'"
ADD after NAMED --'WEKpurosot'--

Signed and Sealed this

First Day of July, 2008

JON W. DUDAS
*Director of the United States Patent and Trademark Office*